United States Patent [19]
Boon

[11] Patent Number: 5,796,059
[45] Date of Patent: Aug. 18, 1998

[54] PRESSURE-SENSITIVE SWITCH APPARATUS

[76] Inventor: Stephen W. Boon, 215 Hazardville Rd., Longmeadow, Mass. 01106

[21] Appl. No.: 617,608

[22] Filed: Mar. 19, 1996

[51] Int. Cl.⁶ .......................... H01C 10/10; H01H 35/00
[52] U.S. Cl. ........................................ 200/85 R; 338/114
[58] Field of Search ..................... 200/5 A, 5 B, 200/5 E, 85 R, 85 A, 86 R, 86 A, 511, 512–517; 340/543–545, 666; 338/99, 114, 118, 42

[56] References Cited

U.S. PATENT DOCUMENTS

| | | | |
|---|---|---|---|
| 3,879,586 | 4/1975 | Du Rocher et al. | 200/5 A |
| 3,952,173 | 4/1976 | Tsuji et al. | 200/264 |
| 3,960,044 | 6/1976 | Nagai et al. | 200/511 X |
| 4,164,634 | 8/1979 | Gilano | 200/5 A |
| 4,304,991 | 12/1981 | Weber | 200/46 |
| 4,308,439 | 12/1981 | Itoh | 200/5 E X |
| 4,317,012 | 2/1982 | Itoh | 200/5 A |
| 4,390,758 | 6/1983 | Hendrickson | 340/543 |
| 4,500,757 | 2/1985 | Rooney | 200/5 A |
| 4,845,323 | 7/1989 | Beggs | 200/85 R |
| 4,907,845 | 3/1990 | Wood | 200/85 R X |

*Primary Examiner*—J. R. Scott
*Attorney, Agent, or Firm*—Alix, Yale & Ristas, LLP

[57] ABSTRACT

A pressure-sensitive switch apparatus for use in monitoring the position of a patient in a bed or chair is provided. The switch includes a resilient conductor disposed between first and second conductors located at opposite surface areas of the switch. The resilient conductor provides varying degrees of electrical contact between the first and second electrical conductors in response to pressure applied to either of these conductors by shifting of the patient's weight.

16 Claims, 3 Drawing Sheets

PRESSURE-SENSITIVE SWITCH APPARATUS

BACKGROUND OF THE INVENTION

The present invention relates to a pressure-sensitive switch apparatus and, more particularly, to such an apparatus for use in monitoring the presence of a patient in a bed or chair.

A problem of considerable concern to health care providers is that of patients leaving a bed or chair when the patient is not safely ambulatory. The use of restraints to ensure the safety and well-being of such patients is becoming impracticable in many instances, not only because of legal issues relating to patients' rights, but also because of a change to a more considered approach by medical and nursing staff toward patients. Concerns regarding the use of restraints are even more acute in the case of home care where patients are typically cared for by family members.

There is a need, therefore, for a less invasive approach to monitor patients restricted to a bed or chair and to alert health care care providers when patients attempts movement on their own.

It is, therefore, an object of the invention to provide a simple and reliable electronic device which automatically alerts nursing staff or other care givers should a patient attempt to exit a bed or chair unattended.

It is further object of the invention to provide such a device which can be utilized in combination with standard monitoring devices such as home security systems.

It is a still further object of the invention to provide such a device which can be used with commercially available equipment which permits the sensitivity of the device to be adjusted to optimize the performance of the device.

SUMMARY OF THE INVENTION

The invention meets these and other objects by providing a pressure-sensitive switch apparatus which is positioned beneath a patient lying or sitting in a bed or sitting in a chair. While the switch may be placed directly under the patient, it is preferably placed under or in the mattress or chair cushion or beneath a covering for the mattress or cushion. When the patient is present in the bed or chair, the patient's weight provides sufficient pressure to cause the switch to remain closed. On the other hand, when the patient attempts to exit the bed or chair, the resulting reduction of pressure applied to the switch causes it to open and alert nursing staff or other care givers that the patient is attempting movement on his or her own.

A pressure sensitive switch apparatus embodying the invention includes a first electrical conductor, a second electrical conductor, and a resilient electrical conductor disposed between the first and second conductors. A substantially non-conductive member disposed between the resilient electrical conductor and either the first and second electrical conductors has at least one passageway which permits the passage of at least a portion of the resilient conductor in response to pressure applied to at least one of the first and second conductors. When sufficient pressure is applied to one of the first or second conductors, the resilient conductor is forced through the passageway and contacts the other of the conductors, thus establishing a closed electrical circuit between the first and second conductors.

In practice, when the patient is present in the bed or chair, the patient's weight applies sufficient pressure to the first or second conductor to force the resilient conductor through the passageway and close the circuit. When the patient attempts to leave the bed or chair and pressure is reduced on the switch, the resilient conductor moves back through the passageway and the circuit opens. The opening of the circuit causes activation of an associated monitoring device, which may be a standard home security system, connected with the pressure-sensitive switch through associated electronic circuitry to alert the care giver that the patient is attempting movement on his or her own. The operation of the switch is enhanced by connecting the switch to existing monitoring equipment that contains controls which enable the user to select a specific desired pressure for activation. This enables the switch to be employed for determining if the patient is in a seated position versus a prone position which can be critical in, for example, a hospital trauma unit.

DETAILED DESCRIPTION

Figure 1:
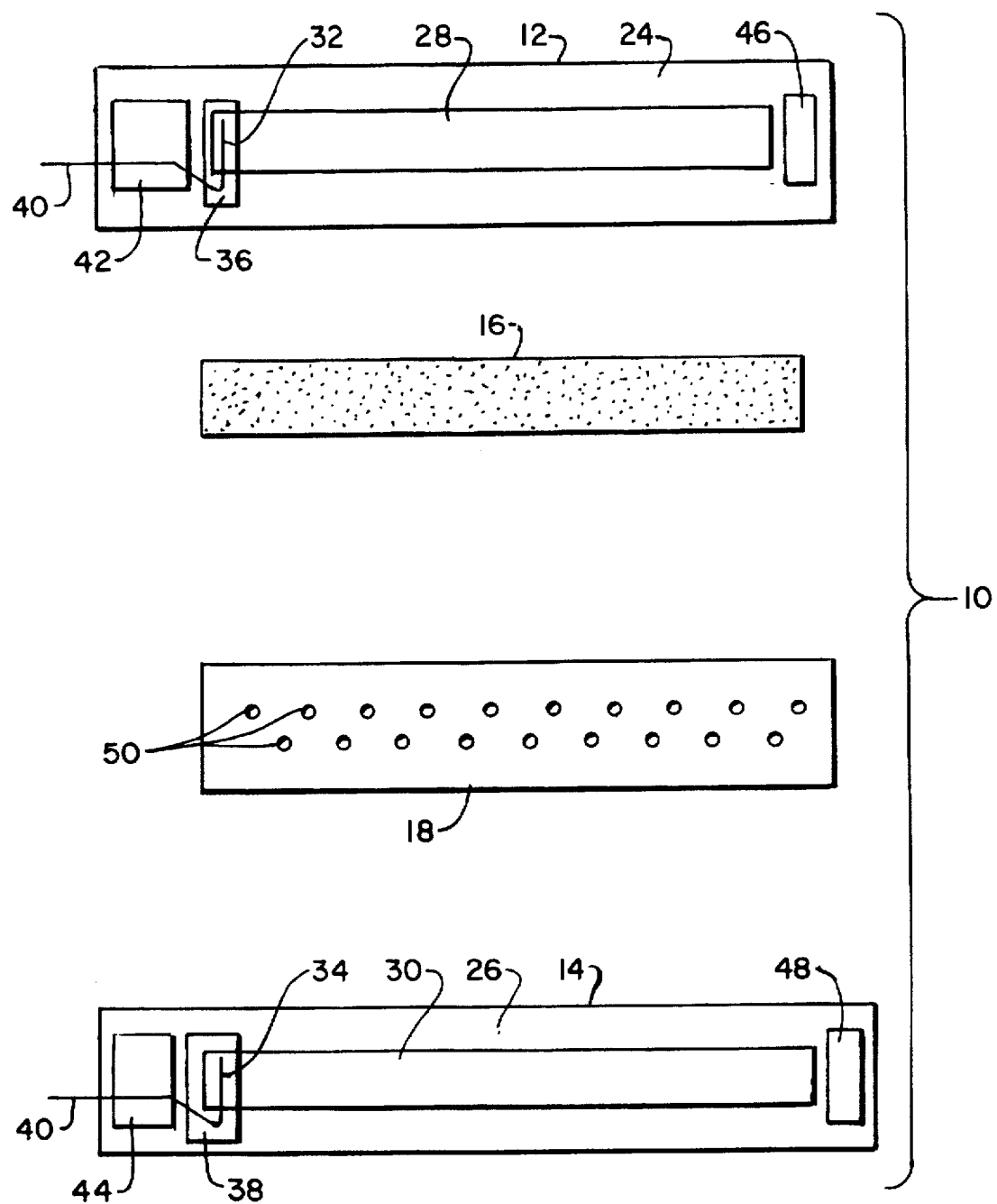
FIG. 1 is an exploded plan view of a pressure-sensitive switch embodying the invention.
Figure 2:
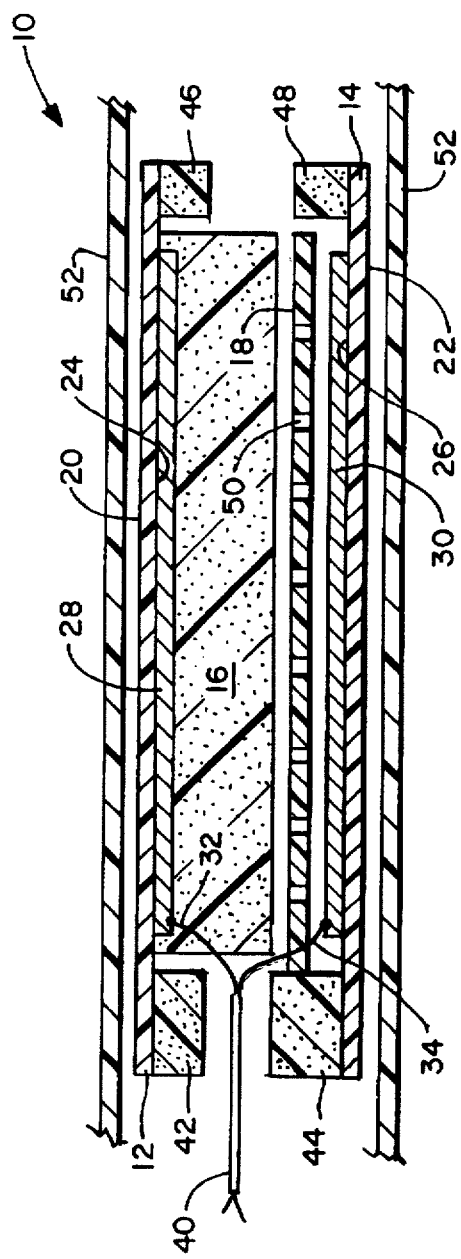
FIG. 2 is a cross-sectional view, partly exploded, of the switch shown in FIG. 1.

Referring to FIGS. 1 and 2, a pressure-sensitive switch, generally indicated 10, embodying the invention includes a first base member 12, a second electrical conductor 14, a resilient base member 16 and a substantially non-conductive member 18.

The base members 12 and 14 are formed from a non-electrically conductive, thin, flexible material. Preferably, this material is high-density polyethylene, although it should be understood that the invention is in no way limited in this regard and that a wide range of other non-conductive, flexible materials may be used. The base members 12 and 14 are generally of rectangular configuration, and in the illustrated embodiment measure about 0.023 inches thick, 3.500 inches wide and from about 4 to about 26 inches long, depending on whether the switch is used for a chair or bed.

Each of the base members 12 and 14 has, respectively, an outer surface 20 and 22 and an inner surface 24 and 26. A conductive path 28 is processed on the inner surface 24 of base member 12, and conductive path 30 is processed on the inner surface 26 of base member 14. While the conductive paths 28 and 30 may be hard wired in a conventional manner, in the preferred embodiment they are formed from a conductive, carbon graphite ink or paint which is silk-screened or otherwise uniformly applied to the inner surfaces 24 and 26. The ink is combined with an acetate to enhance adhesion of the ink to the polyethylene, and with the ink in place, a conductive value is maintained regardless of bending or twisting of the base members 12 and 14.

In the illustrated embodiment, conductive paths 28 and 30 are from about 0.001 to about 0.003 inches thick, about 1.500 inches wide and from about 4 to about 20 inches in length. The conductive paths are placed about 1 inch from either side of base members 12 and 14, and about 2.500 inches from the left end of the switch apparatus 10 as shown in FIGS. 1 and 2 and about 1.500 inches from the opposite end of 15 and 23 base members. Of course, the dimensions of the ink path can be altered depending on the dimensions of the switch.

Conductive wires 32 and 34 are adhered to the conductive paths 28 and 30, respectively, by adhesive areas 36 and 38. The wires are insulated close to the conductive paths to prevent contact with other conductive components of the switch apparatus and are jacketed to form a cable 40 to exit the switch apparatus. The cable 40 is adhered in place by two pads of adhesive polyethylene foam 42 and 44 mounted on inner surfaces 24 and 26, respectively. The foam pads are adhesive on all sides and surround the exiting cable to provide strain relief. In addition, the adhesive pads 42 and 44 provide bonding between conductors 12 and 14. In the preferred embodiment of the invention, the pads 42 and 44 are 0.062 inches thick, about 2.0 inches wide and about 2.0 inches long. Two more adhesive pads 46 and 48 are provided at the opposite end of the switch apparatus 10 to provide additional areas of bonding between the base members 12 and 14. In the preferred embodiment, the pads 46 and 48 are about 0.062 thick and measure about 0.75 inches in width and about 2.0 inches in length. Of course, other means for securing the wires 32 and 34 to the conductive paths and for bonding the base members 12 and 14 to one another could be substituted for the adhesive areas 36 and 38 and the adhesive pads 42–48 without departing from the scope of the invention.

As shown best in FIG. 2, when the switch apparatus is in its assembled condition, the resilient conductor 16 is disposed adjacent to and in contact with the conductive path 28. Accordingly, electric current applied to the conductive path 28 via the conductive wire 32 is transferred to the resilient conductor 16. In the preferred embodiment of the invention, the resilient conductor is formed from a conductive foam which is adhered directly to the base member 12 outside the area covered by the conductive path 28 by a thin layer of adhesive (not shown). The conductive foam provides consistent surface and volume resistivities and is commercially available from Foam Tech Inc. The foam comprises a homogenized mixture of carbon and polyethylene which is cellular in construction and about 0.125 inches thick when uncompressed. When pressure is applied, the conductive foam compresses, condensing the cellular construction. Electrically, this causes the carbon elements to condense, thus densifying the conductive carbon structure and allowing more electrical current to pass than when the foam in uncompressed.

Effectively, the foam is a variable resistor that responds to the pressure being applied. The more pressure that is applied, the more the foam condenses and the lower its resistive value allowing more current to pass through the area of the foam that is compressed. The lower the pressure that is applied to the foam, the less it is compressed and the higher its resistive value. Thus, a patient weighing 200 pounds sitting or laying on top of the switch apparatus would cause more electrical current to flow than would a patient weighing 100 pounds. In the illustrated embodiment, the resilient resistor 16 measures about 2 inches in width and about 20.0 inches in length. Again, the length varies from about 4 to about 20 inches depending if the switch apparatus is utilized for a bed or a chair.

Attached to base member 14 by means of adhesive is the non-conductive member 18. Member 18 is formed from a non-conductive, thin, flexible material which in the preferred embodiment is polyvinyl chloride. The material is about 0.010 thick, 3.500 inches wide and 4 to 20 inches in length. The non-conductive member 18 includes a plurality of apertures or openings 50, 50 which provide a passageway for the conductive foam when pressure is applied to the outer surface 20 or 22 of base members 12 and 14, respectively.

That is, if the patient's weight applies sufficient pressure to, for example, outer surface 20, the conductive foam is forced through one or several of the apertures 50 and contact is made with conductive path 30 on base member 14. Thus, a closed electrical circuit is established between the two conductive paths 28 and 30 through the foam conductor 16. When the pressure is released and the resilient foam retracts through the apertures 50, 50 the circuit is opened. In the illustrated embodiment, the apertures 50, 50 are about 0.190 inches in diameter and 0.010 in height, which are the preferred dimensions based on the weight of adolescent and adult patients, as apertures having these dimensions provide the appropriate amount of contact between the foam conductor 16 and the conductive paths 28 and 30. The switch can be adapted to monitor patients of lower weight, such as young children and infants, simply by enlarging the apertures 50, 50 allowing more of the foam to pass more easily therethrough, while at the same time requiring less pressure.

Figure 3:
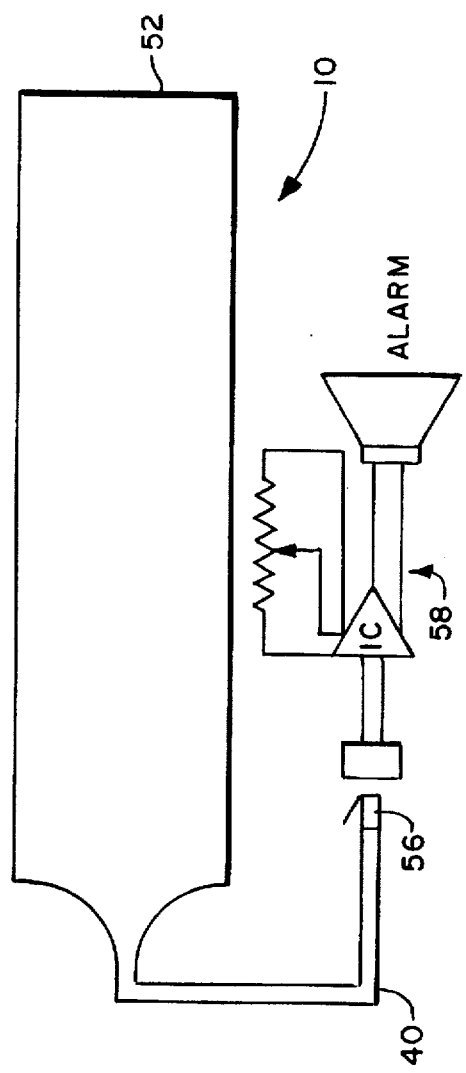
FIG. 3 is a top plan view of the switch shown in FIG. 1 with a protective cover in place.

The switch apparatus 10 is entirely enclosed in a vinyl covering 52, as shown in FIGS. 2 and 3. The cover is slightly larger in width and longer in length than the switch 10 to accommodate mounting holes 54. One end is tapered to allow cable 40 enclosing conductive wires 32 and 34 to exit the switch. The covering is made from a thin, flexible medical grade polyvinyl chloride about 0.012 thick, 3.750 inches wide and 4 to 28 inches long. A beading surrounds the covering where each side has been wielded to form the covering.

As shown in FIG. 3, the cable 40 terminates with a connector 56 to facilitate hook-up and operation of an electronic control 58. The control 58 monitors the variable resistive values of the conductive foam in response to pressure applied to and removed from the switch apparatus. With the switch apparatus 10 in place on, in or under a bed mattress or chair cushion, the control 58 is able to monitor shifting or other movement of the patient to a position that places the patient in potential danger of injury.

As noted above, conventional monitoring equipment allows the sensitivity of the control 58 to be adjusted so that early warning of patient movement is provided. In addition, the sensitivity of the control 58 can be adjusted to compensate for the weight of the mattress, overlays or other bedding or distortions of the switch created by a patient laying or sitting on the switch while it is supported on an uneven surface.

In practice, the switch is designed to remain open absent the presence of the patient in the bed or chair. When the patient is a proper laying or sitting position, the switch is closed. When the patient rises from the bed or chair or, based on the sensitivity setting, even shifts his or her weight to attempt such motion, the conductive foam retracts through the apertures 50, 50 to cause an open condition and sound an alarm through the control 5.

Figure 4:
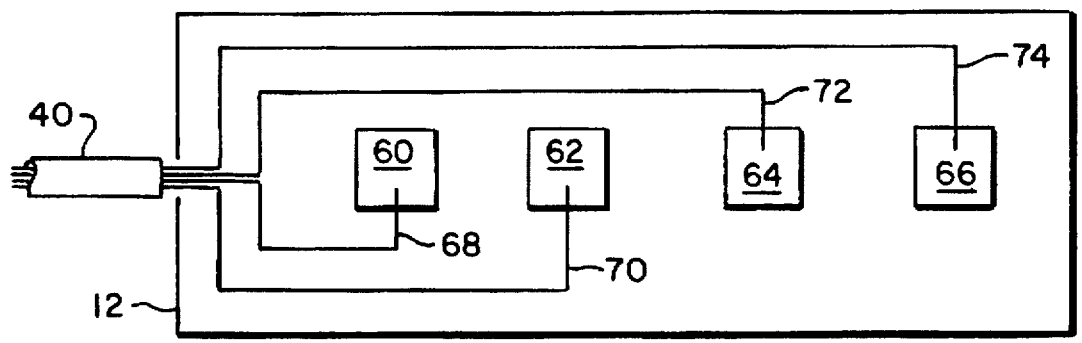
FIG. 4 is a plan view of a second embodiment of a pressure-sensitive switch made according to the invention.

An alternative embodiment of the switch apparatus is shown in FIG. 4, in which components corresponding to those shown in the first embodiment have been given like numbers. In the FIG. 4 embodiment of the switch apparatus 10', the conductive path supported by the base member 12 is formed as a series of segments 60, 62, 64 and 66. Each of these segments has a separate conductive wire 68, 70, 72 and 74, respectively, supplied from the cable 40, and each of the conductive wires is monitored by separately by the control (not shown). The non-conductive member 18, the conductive path 30 and the base member 14 remain unaltered from the embodiment illustrated in FIGS. 1–3. Dividing the conductive path into a series of segments provides enhanced sensing of the patient's position, since the switch can be constructed so that individual segments are located beneath specific body parts. Accordingly, the position of a particular body part can be monitored while the patient lays or sits in a normal resting position. Having an individual sensor for a particular body part is especially important in, for example, head injury cases where a patient's head shifts to a medically compromising position while the patient lays in an otherwise normal resting position.

While the invention has been described as it pertains to use in a patients bed or chair, in a hospital, nursing home or in the individual home setting, it can be seen that the invention can be for any other switching purpose where a variable pressure operating switch could be utilized. While the invention has been described with a certain degree of particularity, it is manifest that many changes may be made in the construction and arrangement of -components without departing from the spirit and scope of this disclosure. It is understood that the invention is not limited only by the scope of the attached of the attached claim or claims, including the full range of equivalency to which each element thereof is entitled.

I claim:

1. A pressure-sensitive switch apparatus comprising:
   a first electrical conductor;
   a second electrical conductor;
   a resilient electrical conductor disposed between the first and second conductors, said resilient conductor comprising a variable resistor, wherein the resistive value of said resilient conductor is inversely proportional to the pressure applied to said resilient conductor; and
   a substantially non-conductive member disposed between the resilient electrical conductor and one of the first and second electrical conductors and defining at least one passageway for the passage of at least a portion of the resilient conductor therethrough in response to pressure applied to at least one of the first and second conductors to establish a closed electrical circuit between the first and second conductors.

2. The switch apparatus of claim 1 wherein the first conductor comprises at least one member having an outer surface and an inner surface, and a first electrically conductive path supported on the inner surface of the first member.

3. The switch apparatus of claim 1 wherein the second conductor comprises at least one member having an outer surface and an inner surface, the inner surface having a second electrically conductive path supported thereon.

4. The apparatus of claim 1 wherein the resilient, electrical conductor is disposed between the first conductor and the substantially non-conductive member.

5. The switch apparatus of claim 1 wherein the first conductor comprises a thin, flexible member having an outer surface and an inner surface and a conductive pathway supported on the inner surface.

6. The switch apparatus of claim 1 wherein the second conductor comprises a thin, flexible member having an outer surface and an inner surface and a conductive pathway supported on the inner surface.

7. The switch apparatus of claim 1 wherein the substantially non-conductive member comprises a thin flexible sheet of substantially non-conductive material defining at least one aperture.

8. The switch apparatus of claim 1 wherein the resilient conductor comprises a resilient, conductive sheet material.

9. The switch apparatus of claim 8 wherein the sheet material is a conductive foam.

10. The switch apparatus of claim 1 further comprising at least one electrical connector mounted on the first and second conductors.

11. The switch apparatus of claim 1 further comprising a substantially non-conductive flexible cover surrounding the first, second and resilient conductors and the substantially non-conductive member.

12. The switch apparatus of claim 5 wherein the first conductor comprises a plurality of said members, at least one of the first and second conductors comprises a plurality of individual members.

13. A pressure-sensitive apparatus comprising:
   a first conductor including a thin, flexible member having an outer surface and an inner surface and an electrically conductive path mounted on the inner surface;
   a second conductor including a thin, flexible member having an outer surface and an inner surface;
   a thin, flexible, resilient electrical conductor disposed adjacent to the inner surface of the first conductor, said resilient conductor comprising a variable resistor, wherein the resistive value of said resilient conductor is inversely proportional to the pressure applied to said resilient conductor; and
   a thin, flexible, substantially non-conductive member disposed adjacent to the inner surface of the second conductor defining a plurality of apertures for the passage of at least a portion of the resilient conductor therethrough in response to pressure applied to at least one of the first and second conductors.

14. The switch apparatus of claim 13 further comprising at least one electrical connector mounted on the first and second conductors.

15. The switch apparatus of claim 13 further comprising a thin, flexible, substantially non-conductive cover surrounding the first, second and resilient conductors and the substantially non-conductive member.

16. The switch apparatus of claim 1 further comprising:
   means for transmitting signals indicative of the degree of electrical contact between the first and second electrical conductors; and
   means for monitoring the transmitted signals and providing an output corresponding to the degree of contact between the first and second conductors.

* * * * *